US000001376H

United States Statutory Invention Registration [19]

[11] Reg. Number: H1376

[43] Published: Nov. 1, 1994

Osborn, III et al.

[54] CAPACITY INDICIA FOR ABSORBENT ARTICLES

[76] Inventors: Thomas Osborn, III; Nona J. Redwine, both of 6100 Center Hill Rd., Cincinnati, Ohio 45224

[21] Appl. No.: 982,131

[22] Filed: Nov. 24, 1992

Related U.S. Application Data

[62] Division of Ser. No. 539,779, Jun. 18, 1990, abandoned.

[51] Int. Cl.[5] ..... A61F 13/42

[52] U.S. Cl. ..... 604/361; 604/385.1

[58] Field of Search ..... 604/361, 385.1

[56] References Cited

U.S. PATENT DOCUMENTS

| | | | |
|---|---|---|---|
| 2,296,341 | 2/1939 | Fourness | 604/375 |
| 3,400,717 | 9/1968 | Cubitt et al. | 128/284 |
| 3,651,809 | 3/1972 | Champaigne, Jr. | 128/290 |
| 3,675,654 | 7/1972 | Baker et al. | 604/361 |
| 3,860,002 | 1/1975 | Kolbach | 128/284 |
| 3,968,798 | 7/1976 | Hokanson | 128/284 |
| 4,184,498 | 1/1980 | Franco | 604/375 |
| 4,212,302 | 7/1980 | Karami | 128/287 |
| 4,231,370 | 11/1980 | Mroz et al. | 604/361 |
| 4,285,343 | 8/1981 | McNair | 604/385.1 |
| 4,333,463 | 6/1982 | Holtman | 128/287 |
| 4,381,782 | 5/1983 | Mazurak et al. | 604/368 |
| 4,443,512 | 4/1984 | Delvaux | 428/162 |
| 4,507,121 | 3/1985 | Leung | 604/361 |
| 4,623,340 | 11/1986 | Luceri | 604/385 R |
| 4,705,513 | 11/1987 | Sheldon et al. | 604/361 |
| 4,804,379 | 2/1989 | Toth et al. | 604/378 |

FOREIGN PATENT DOCUMENTS

| | | | |
|---|---|---|---|
| 2124907A | 2/1984 | United Kingdom | A61F 5/44 |
| 8604219 | 7/1986 | WIPO | 604/361 |
| 9119471 | 12/1991 | WIPO | 604/361 |

OTHER PUBLICATIONS

New Freedom Brand Maxi and Super Maxi pads sold by Kimberly-Clark Corporation.

*Primary Examiner*—David Brown

[57] ABSTRACT

Disclosed are indicia for use in conjunction with the core of an absorbent article, such as a sanitary napkin, disposable diaper, or adult incontinence product. The indicia are absorbent or liquid pervious to obviate reduction in the target area for loading of the absorbent core of such product. The indicia provide a means for visually indicating to the wearer incipient failure of the core when the capacity of the core may be exceeded by lateral migration of liquids deposited on the absorbent core. The indicia may be separate or integral relative to the absorbent core.

7 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CAPACITY INDICIA FOR ABSORBENT ARTICLES

This is a division of application Ser. No. 07/539,779, filed on Jun. 18, 1990, now abandoned.

FIELD OF THE INVENTION

This invention is directed to a means for indicating when an absorbent core is loaded to a level such that its capacity may be exceeded, and alerting the wearer or caretaker to the potential failure of the absorbent core upon additional loading. More particularly, this invention is directed to indicia which visually indicate when the capacity of an absorbent core used to collect and contain bodily discharges is about to be exceeded.

BACKGROUND OF THE INVENTION

Absorbent cores used to collect and contain bodily discharges are well known in the art. Absorbent cores are used in conjunction with disposable absorbent articles such as sanitary napkins, disposable diapers, and multi-component adult incontinence garments to collect and contain such discharges, which are typically liquid. Such articles may be disposable, reusable, integral, releasable and intended for wear by infants or adults.

The wearer of any articles utilizing an absorbent core, or the caretaker of a wearer, may become frustrated or irritated if the capacity of the absorbent core is exceeded, i.e., loading beyond that which can be absorbed by the core occurs and the core fails, i.e., bodily discharges are not contained by the core. Such discharges may run off the core and be transported outside the boundaries of the sanitary napkin, diaper, adult incontinence garment, or other absorbent article, and may soil the clothing or bedding of the wearer.

Typically, the total capacity of an absorbent core is not utilized prior to failure occurring and the core is theoretically able to collect and contain additional loadings of discharges when failure occurs. Failure often occurs because of lateral migration of deposited liquid bodily discharges. The discharges deposited on the absorbent core may laterally migrate to either longitudinal side margin of the absorbent core, particularly if such discharges are not deposited coincident with (or even near) the longitudinal centerline of the absorbent core. Upon failure, further loading of discharges does not penetrate the core and become absorbed thereby, but rather becomes run-off and breaches the longitudinal side margins of the article which utilizes such a core.

Several attempts have been made in the art to guard the longitudinal side margins of absorbent articles from lateral run-off of deposited liquids. For example, some sanitary napkins have been provided with liquid impervious partitions which overlay the core. Such liquid impervious partitions may be interposed between the absorbent core and the topsheet or may overlay the topsheet. In either embodiment, however, the partitions reduce the effective target area of the absorbent core. This occurs due to liquids deposited on the partitions usually do not penetrate to the core. Instead, the liquids deposited onto the partitions run, along the outside of the partitions, through and past the longitudinal side margins of the absorbent core, and breaches the absorbent article associated with the absorbent core.

Another attempt in the art to notify the wearer or caretaker that an absorbent garment is nearing its capacity and ready to be changed is a wetness indicator. A wetness indicator, such as the type disclosed in U.S. Pat. No. 4,231,370 issued Nov. 4, 1980 to Mroz et al., typically reacts to the pH of discharged bodily fluids by changing color. However, such wetness indicators are typically applied to the inwardly oriented face of a transparent backsheet and do not react to notify the wearer or caretaker of loading, unless the core is loaded substantially throughout its thickness. Thus, discharged body fluids which are not absorbed into the thickness of the core will fail to register with a wetness indicator on or adjacent the face of the absorbent core opposed to the wearer. Also, such wetness indicators impose opacity limitations on the selection of the backsheet material.

Typically, the absorbent core of such articles is rectangularly shaped, for ease of manufacturing. However, there is frequently a wearer preference for an absorbent core which is narrower at the center than at the ends, to comfortably accommodate the legs, and obviate or minimize occurrences of bunching or wadding of the core. Such wearer preference is more frequently encountered when the absorbent core is utilized in conjunction with a sanitary napkin.

Accordingly, it is an object of this invention to provide an absorbent core and a means for indicating the incipiency of a frequent mode of failure, i.e. lateral run-off from the absorbent core, is about to occur. It is also an object of this invention to provide a means for visually indicating when the capacity of an absorbent core is about to be exceeded. It is further an object of this invention to visually indicate incipient failure of the core without reducing its target area. Finally, it is an object of this invention to provide visually discernible indicia which enhance the apparent shape of the absorbent core to the wearer.

BRIEF SUMMARY OF THE INVENTION

The present invention comprises a disposable absorbent article, such as a diaper, sanitary napkin, or adult incontinence product. The disposable absorbent article has a longitudinal centerline, and two longitudinal side margins and comprises a liquid pervious topsheet, a liquid impervious backsheet at least partially peripherally joined to the topsheet, an absorbent core between the topsheet and the backsheet, and a liquid pervious, preferably absorbent, means for visually indicating when absorbed liquid has approached the longitudinal side margins of the disposable absorbent article.

The liquid pervious or absorbent means for indicating the approach of liquids to the longitudinal side margins of the article may oomprise two visually discernible indicia, with one indicium being disposed along each longitudinal side margin of the absorbent article. The indicia may be parallel the longitudinal centerline or may be concave towards the longitudinal centerline. The indicia may comprise a partition between the core and the topsheet or a dye applied to the topsheet, backsheet, or core, or may be separate strips outboard of the core, may represent a difference in apparent elevation between the core and the indicia.

The indicia may be separate from or integral with the absorbent core. The indicia may be the same color as the absorbent core or may contrast in color with the absorbent core. The indicia may be of the same thickness as the absorbent core or be of a different thickness than the absorbent core.

BRIEF DESCRIPTION OF THE DRAWINGS

While the Specification concludes with claims particularly pointing out and distinctly claiming the present invention, it is believed the invention will be better understood from the following description taken in conjunction with the accompanying drawings wherein like components are designated by the same reference numeral, analogous articles are designated with a prime symbol, and:

DETAILED DESCRIPTION OF THE INVENTION

Figure 1:
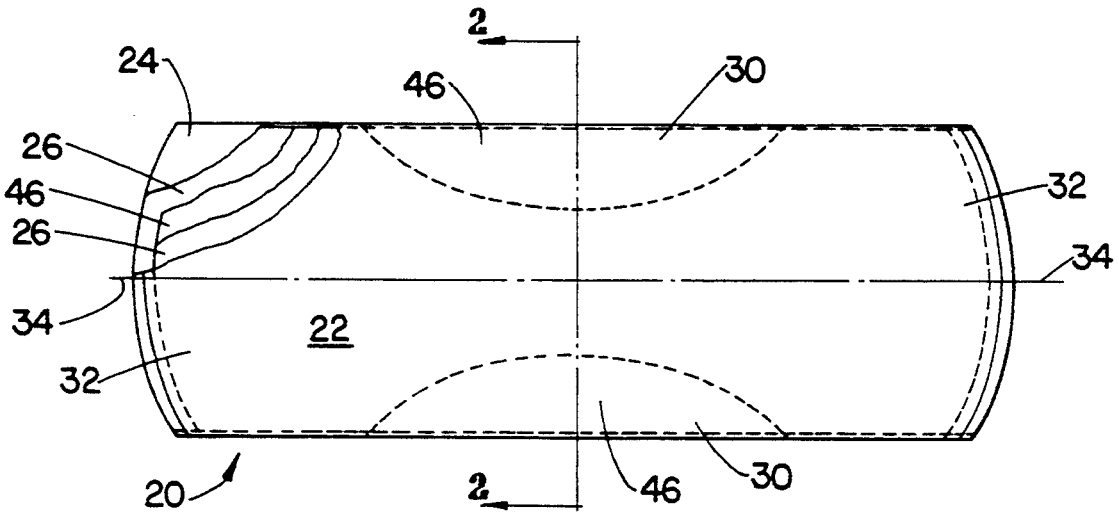
FIG. 1 is a top plan view, shown partially in cutaway, of a sanitary napkin according to the present invention.

Referring to FIG. 1, the indicia 46 may comprise any means for indicating when the absorbent article is approaching its capacity, and alerts the wearer, or the caretaker, to the need for removing the disposable absorbent article before significant additional loading occurs. Any means for visually indicating to the user when the loading is approaching the lateral side margins 32 of the core 26 is suitable.

Preferably, the indicia 46 are absorbent, so that the target area of the core 26 is not reduced. However, indicia 46 which are liquid pervious and allow liquids deposited on top of the indicia 46 to penetrate therethrough to the absorbent core 26 are suitable.

Components, such as indicia 46, are considered "liquid pervious" if such components allow liquids to pass therethrough without significantly retarding or obstructing the transmission of such liquids therethrough. Components are considered "absorbent" if such components not only transmit such liquids, but also can retain a portion of the liquids deposited on such components. Thus it will be apparent that all absorbent components are liquid pervious, but not all liquid pervious components are absorbent.

Any indicia 46 which are readily visually distinguishable from the core 26 are suitable, so long as there is no significant obstruction to the transmission of liquids deposited thereon to the absorbent core 26. If the indicia 46 are not liquid pervious or are not absorbent, deposited liquids may laterally transport to the longitudinal side margins 30, whereupon failure and exposure to the clothing or bedding may occur.

Preferably, the indicia 46 are shaped convex towards the longitudinal centerline 34. This arrangement provides the advantage that the indicia 46 will present a shaped appearance even when used with a rectangularly shaped absorbent core 26. Thus, the disposable article, sanitary napkin 20, diaper 20', or adult incontinence product may have both the benefits of a rectangularly shaped core 26 for ease of manufacturing and the benefits of a tapered appearance as the lateral centerline is approximated to meet consumer preferences. However, the indicia 46, if desired, may be straight or concave towards the longitudinal centerline 34.

If desired, the indicia 46 may be visually or tactilely discernible from the absorbent core 26. Preferably the indicia 46 are visually discernible from the absorbent core 26 through a differing, contrasting color. Typically the absorbent core 26 of most articles is white. Indicia 46 which are pastel colored, yet darker than the typical fluff, cellulose fiber-AGM absorbent core 26 material is suitable. The indicia 46 should be visually discernible through any topsheet 22 which may be utilized in conjunction with the absorbent core 26. When the absorbent core 26 becomes loaded, it may appear somewhat darker than when it is unused. The indicia 46 should contrast sufficiently with the absorbent core 26 under heavily loaded conditions, so that even under such conditions the user or caretaker can tell the capacity of the absorbent core 26 is being approached. The indicia 46 may present a different topography or may contrast in other manners detectable by the wearer or caretaker.

Referring to FIG. 1, in one execution, the invention comprises a disposable absorbent article, particularly a sanitary napkin 20. The sanitary napkin 20 is used to collect vaginal discharges, such as menses, and prevent soiling of the wearer's clothing by such discharges. The sanitary napkin 20 features a liquid pervious topsheet 22, a liquid impervious backsheet 24, an absorbent core 26 intermediate the topsheet 22 and the backsheet 24. The perimeter of the sanitary napkin 20 is defined by two longitudinal side margins 30 and two lateral side margins 32. The sanitary napkin 20 has the indicia 46 disposed along, adjacent or juxtaposed with each longitudinal side margin 30 for visually indicating when the absorbent core 26 is nearly fully loaded.

Figure 3:
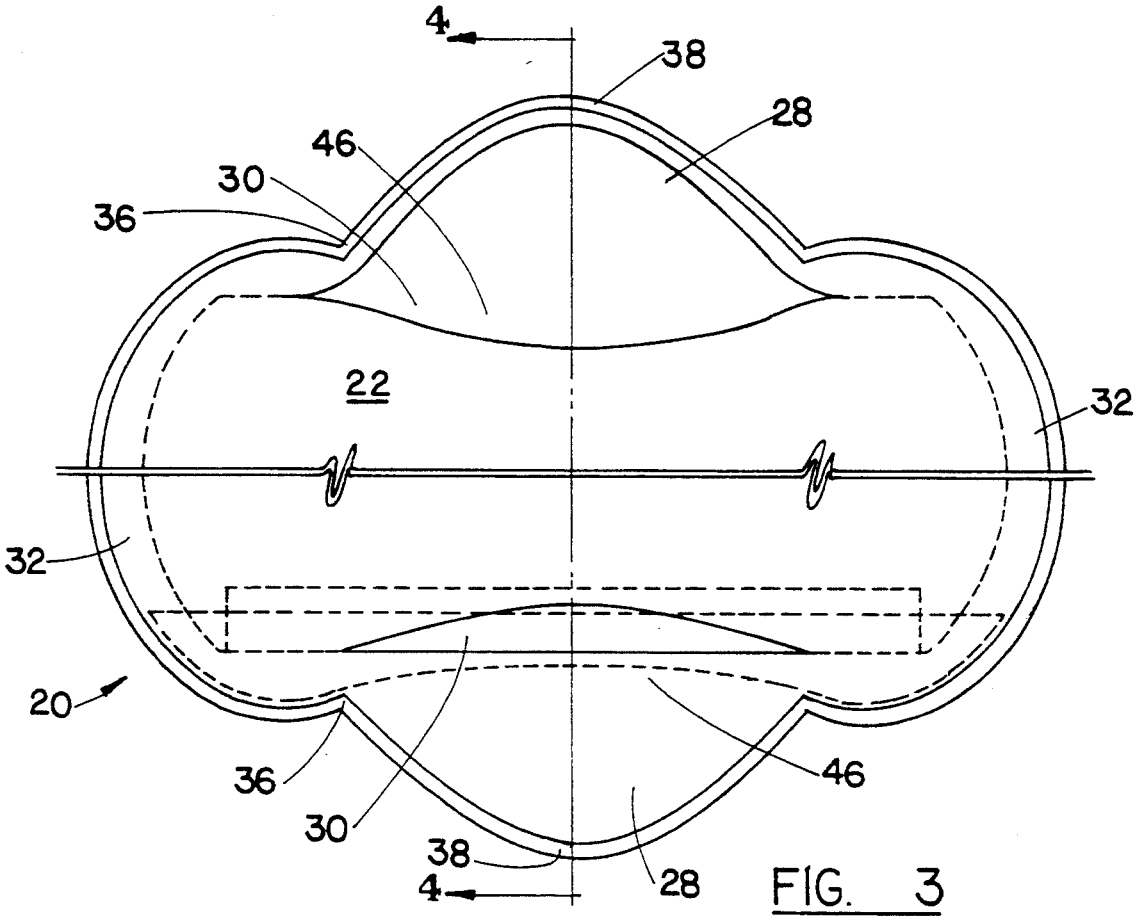
FIG. 3 is a top plan view of a sanitary napkin according to the present invention having flaps.

Referring to FIG. 3, the sanitary napkin 20 may have at least one flap 28 extending from a longitudinal side margin 30 of the sanitary napkin 20, and preferably two symmetrically opposite flaps 28, one extending from each longitudinal side margin 30 of the sanitary napkin 20. The sanitary napkin 20 may have means, such as adhesive, for releasably affixing the sanitary napkin 20 to the undergarment of a wearer.

Referring back to FIG. 1, the sanitary napkin 20 and absorbent core 26 have a longitudinal centerline 34 which conceptually divides the sanitary napkin 20 into two substantially symmetrically opposite halves. As used herein the term "longitudinal" refers to an imaginary line, axis or direction of the absorbent core 26, which line, axis or direction is typically centered between the longitudinal side margins 30 of the absorbent core 26 and is generally aligned with the vertical plane which bisects a standing wearer into left and right body halves. The term "lateral" refers to an imaginary line, axis or direction generally orthogonal the longitudinal direction, within the plane of the absorbent core 26, and is generally sideways aligned relative to the wearer.

Examining the components of this execution of the invention in more detail with continuing reference to FIG. 1, the topsheet 22 is the component of the garment which is oriented towards and contacts the body of the wearer, and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be sanitary, clean in appearance and somewhat opaque to hide the bodily discharges collected in and absorbed by the core 26.

The topsheet 22 should further exhibit good strike-through and rewet characteristics, permitting bodily discharges to rapidly penetrate the topsheet 22 to the core 26, but not flow back through the topsheet 22 to the skin of the wearer. Suitable topsheets 22 may be made from nonwoven materials or perforated polyolefinic films.

The topsheet 22 has a plurality of apertures to permit liquids deposited thereon to pass through to the core 26. Such apertures may, but need not, be present in the flaps 28. An apertured polyolefinic film topsheet 22 having about 5 to about 60 percent open area, typically about 25 percent open area, and a thickness of about 0.01 to about 0.05 millimeters prior to aperturing and about 0.42 to about 0.51 millimeters after aperturing is suitable.

If desired, the topsheet 22 may be sprayed with a surfactant to enhance liquid penetration to the core 26. The surfactant is typically nonionic and should be non-irritating to the skin. A surfactant density of about 0.01 milligrams per square centimeter of topsheet 22 area is suitable. A suitable surfactant is sold by the Glyco Chemical, Inc. of Greenwich, Connecticut as Pegosperse 200 ML.

A particularly suitable topsheet 22 may be made in accordance with U.S. Pat. No. 4,342,314 issued Aug. 3, 1982 to Radel et al. and U.S. Pat. No. 4,463,045 issued Jul. 31, 1984 to Ahr et al., which patents are incorporated herein by reference for the purpose of disclosing particularly preferred executions of liquid pervious topsheets. A topsheet 22 made of model X-3265 or model P1552 apertured formed film sold by the Tredegar Corporation of Terre Haute, Indiana has been found to work well.

The backsheet 24 may be any flexible, liquid resistant, preferably liquid impervious material, such as a polyolefinic film. The backsheet 24 prevents discharges collected by and contained in the sanitary napkin 20, and particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. A low density polyethylene backsheet 24 about 0.01 to about 0.08 millimeters in thickness, preferably about 0.05 millimeters in thickness, has been found to work well. A polyethylene film, such as is sold by the Tredegar Corporation of Terre Haute, Indiana, under model X-813 has been found particularly well suited for the backsheet 24.

Further, the backsheet 24 may be made of a soft clothlike material which is hydrophobic relative to the topsheet 22, e.g., a polyester or polyolefinic fiber backsheet 24 works well. A particularly preferred soft, clothlike backsheet 24 material is a laminate of a polyester nonwoven material lamina and a film such as described in U.S. Pat. No. 4,476,180 issued Oct. 9, 1984 to Wnuk.

In a particularly preferred embodiment, the backsheet 24 is slightly larger than the topsheet 22 and the intermediate absorbent core 26. In such an embodiment, the topsheet 22 and intermediate absorbent core 26 are peripherally circumscribed by the backsheet 24 which has a radial margin of about 0.5 centimeters to about 1.5 centimeters, preferably about 1.0 centimeter, from the side margins of the topsheet 22. This geometry provides a marginal area of protection should the core 26 become overloaded or the sanitary napkin 20 otherwise fail. In such an embodiment the backsheet 24 and flaps 28 are preferably unitary and coextensive.

The topsheet 22 and the backsheet 24 are preferentially peripherally joined using known techniques, either entirely so that the entire perimeter of the sanitary napkin 20 is circumscribed by such joinder or are partially peripherally joined at the perimeter. The term "joined" refers to the condition where a first member or component is affixed, or connected, to a second member or component either directly; or indirectly, where the first member or component is affixed, or connected, to an intermediate member or component which in turn is affixed, or connected, to the second member or component. The joined condition between the first member, or component, and the second member, or component, is intended to remain for the life of the sanitary napkin 20. Conversely, components are considered "removably affixed" if the components may be detached and separated from each other without destruction or unintended gross deformation of either.

Any joined arrangement that provides for capture of the core 26 intermediate the topsheet 22 and the backsheet 24 and a unitary assembly is suitable. Such an assembly has two mutually opposed major faces, one defined by the topsheet 22 and one defined by the backsheet 24.

The outwardly oriented face of the backsheet 24 may further comprise means for attaching the sanitary napkin 20 to the undergarment of the wearer. Pressure sensitive adhesive has been commonly found to work well for this purpose. Preferably a strip of longitudinally oriented adhesive provides good protection against either the front or the back of the sanitary napkin 20 becoming detached from the wearer's undergarment. The adhesive strip may be continuous or intermittent. A particularly preferred arrangement utilizes two longitudinally oriented strips, one on each side of the longitudinal centerline 34.

The absorbent core 26 is the means for collecting and containing bodily discharges, particularly menses, deposited thereon or which otherwise traverses through the liquid permeable topsheet 22. The core 26 is the component of the sanitary napkin 20 which receives and retains the bodily discharges. The core 26 is conformable and nonirritating to the skin. The core 26 may be rectangularly or hourglass shaped. The perimeter of the absorbent core 26 is defined by two longitudinal side edges and two lateral side edges, which are aligned with the longitudinal and lateral side margins 30 and 32 of the sanitary napkin 20 respectively. The core 26 preferably has two opposed faces, one oriented towards the backsheet 24 and one oriented towards the topsheet 22 and is generally planar, i.e. does not have significant variations in thickness or isolated macroscopic voids.

Suitable materials for the core 26 include combinations of airfelt, such as cellulose wadding, and fibrated communition pulp; layers of tissue paper; and absorbent gelling materials. If a tissue paper core 26 is selected, tissue paper made in accordance with U.S. Pat. No. 4,191,609 issued Mar. 4, 1980 to Trokhan and incorporated herein by reference to show a particularly preferred tissue paper core construction for the sanitary napkin 20 described herein. If it is desired to incorporate absorbent gelling materials into the core 26 of the sanitary napkin 20, absorbent gelling materials made in accordance with U.S. Pat. No. Re. 32,649 issued Apr. 19, 1988 to Brandt et al., and incorporated herein by reference for showing particularly preferred absorbent gelling materials, are suitable. A suitable laminate of absorbent gelling materials and tissue may be purchased from the Grain Processing Corporation of Muscatine, Iowa under Model Number L535.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Illinois.

The core 26 should be sized to register with the topsheet 22 and backsheet 24. For ease of manufacturing, the absorbent core 26 should be rectangularly shaped. However, the absorbent core 26 may have arcuate sides, tapering inwardly as the lateral centerline is approached to provide a generally preferential shaped appearance. The absorbent core 26 may be somewhat dog-bone or hourglass shaped to provide a generally preferred appearance at the expense of manufacturing difficulties. Alternatively, such an appearance may be provided by indicia 46 which are concave towards the longitudinal centerline 34 and overlay the core 26. The core 26 is preferably interposed between the topsheet 22 and backsheet 24 to prevent the absorbent material of the core 26 from shredding or becoming detached while the sanitary napkin 20 is worn and to ensure proper containment of bodily discharges. This arrangement also helps to provide for a unitary assembly.

The sanitary napkin 20 execution of this invention preferably has a caliper of less than about 4 millimeters and more preferably less than about 6 millimeters (0.24 inches), as more measured with a comparator gage having an approximately 80.0 gram test weight, an approximately 10.0 gram comparator foot having a of about 2.54 centimeters and a contact surface area of approximately 5.1 square centimeters. Also, the sanitary napkin 20 of the present invention should have a topsheet 22 surface area of at least about 100 square centimeters to prevent discharged liquids from missing the target area.

The core 26 is preferentially joined to the topsheet 22, and may be joined to the backsheet 24. Joining is preferentially accomplished by adhesive bonding the core 26 to the topsheet 22 or the backsheet 24. Such adhesive (not shown) may be applied in any suitable spray pattern, such as a spiral or longitudinally oriented beads. The adhesive should be surfactant resistant and of low pressure sensitivity, so as not to stick to the skin of the wearer.

Referring to FIG. 3, the sanitary napkin 20 may also comprise a flap 28 extending from a longitudinal side margin 30 of the sanitary napkin 20, and preferably one flap 28 extending from each longitudinal side margin 30 of the sanitary napkin 20. The flaps 28 have a proximal end 36 which is typically coincident with the juncture of attachment of the flap 28 to the longitudinal side margin 30 of the sanitary napkin 20 or, alternatively, the proximal end 36 of the flap 28 may be joined to the sanitary napkin 20 at any other location juxtaposed with the longitudinal side margin 30. The flaps 28 extend laterally outwardly from the sanitary napkin 20 and terminate at a distal end 38 which represents the point of the flap 28 furthest from the longitudinal axis 34 of the sanitary napkin 20.

The flaps 28 may be of any shape desired, with one preferred shape being shown in FIG. 3. The flaps 28 are preferably made in accordance with the teachings of U.S. Pat. Nos. 4,589,876 issued May 20, 1986 to Van Tilburg and 4,687,478 issued Aug. 18, 1987 to Van Tilburg.

The flaps 28 are laterally outboard of the longitudinal centerline 34 and central portion of the sanitary napkin 20. As used herein the phrase "central portion" refers to that part of the sanitary napkin 20 intermediate, particularly laterally intermediate, and defined by the proximal ends 36 of the flaps 28.

The flaps 28 may be comprised of an integral and contiguous extension of the topsheet 22, the backsheet 24, or a laminate of both. Alternatively, the flaps 28 may be made of a separate and independent piece of material joined to the longitudinal side margin 30 of the sanitary napkin 20.

Each flap 28 has one face generally coextensive of the topsheet 22 and a mutually opposed face which may be generally coextensive of the backsheet 24. Faces are considered to be coextensive of the topsheet 22 or backsheet 24 if a line having a lateral component can be drawn from the central portion of the topsheet 22 or the backsheet 24 respectively, crosses a side margin 30 or 32 at the perimeter of the sanitary napkin 20, and intercepts such face.

The flaps 28 preferably have a means for attaching one face of the flap 28 to the wearer's undergarment or to the other flap 28. The attachment means may be pressure sensitive adhesive. If pressure sensitive adhesive is selected, it should be disposed on the face of the flap 28 generally coextensive of the backsheet 24 so that when the flaps 28 are wrapped around the crotch portion of the wearer's undergarment, the adhesive will contact rectangular patch of adhesive on each flap 28, about 25 millimeters $\times$20 millimeters in size works well. Suitable pressure sensitive adhesive is sold by the Anchor Continental, Inc., 3 Sigma Division of Covington, Ohio as 0.02 millimeter pass with Century Adhesive A305-4.

Figure 2:
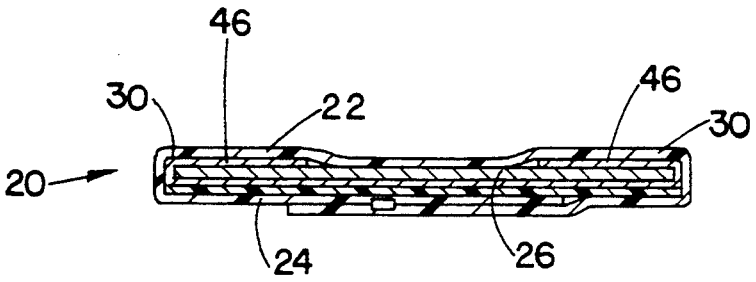
FIG. 2 is a vertical sectional view taken along line 2—2 of FIG. 1 showing a continuous partition type of indicia between the core and the backsheet.

Referring to FIG. 2, in one embodiment the indicia 46 may comprise partitions 46. The partitions 46, like the absorbent core 26, are preferably interposed between, and laterally bounded by, the topsheet 22 and the backsheet 24. However, if the topsheet 22 and absorbent core 26 are laterally narrower than the backsheet 24, the indicia 46 need not be between the topsheet 22 and the core 26, but rather may be outside the topsheet 22, and, if desired, incorporated into the backsheet 24. Alternatively, the indicia 46 may be separate, dedicated components of the disposable absorbent garment 20. The indicia 46 are disposed along and oriented with the longitudinal side margins 30 of the sanitary napkin 20, and more preferably are adjacent the longitudinal edges of the absorbent core 26.

Examining the indicia 46 in more detail, the partitions 46 are made of materials which are absorbent or liquid pervious, and are interposed between the topsheet 22 and the absorbent core 26. The two partitions 46 may be integral, unitary, and connected to each other as an integral member disposed between the absorbent core 26 and the backsheet 24. The partitions 46 should be generally thin, so significant bulk and a nonuniform or nonplanar surface is not presented through the topsheet 22. If desired, the partitions 46 may be treated with a surfactant to promote liquid transmission through the partitions 46 to the absorbent core 26.

Suitable materials for the partitions 46 include tissue, nonwoven fabrics, and apertured formed films. A particularly preferred material for the partitions 46 is tissue having a basis weight of about $2.3\times10^{-3}$ kilograms per square meter (14 pounds per 3,000 square feet) and made according to the teachings of U.S. Pat. No. 3,301,746 issued Jan. 31, 1967 to Sanford et al., which patent is incorporated herein by reference for the purpose of disclosing a particularly preferred partition 46 material. It is to be recognized by one skilled in the art that if the partitions 46 are made of tissue or other absorbent material, the total capacity of the absorbent article 20 is slightly increased. However, if the partition is liquid pervious, such as formed films, no significant addition to the capacity of the absorbent article 20 occurs.

If desired, the partitions 46 may be incorporated into the flaps 28 of a sanitary napkin 20, as illustrated in FIG. 3. Utilizing this arrangement, the partitions 46 may be used in various designs to impart a shaped appearance to the absorbent core 26 of the sanitary napkin 20.

Figure 4:
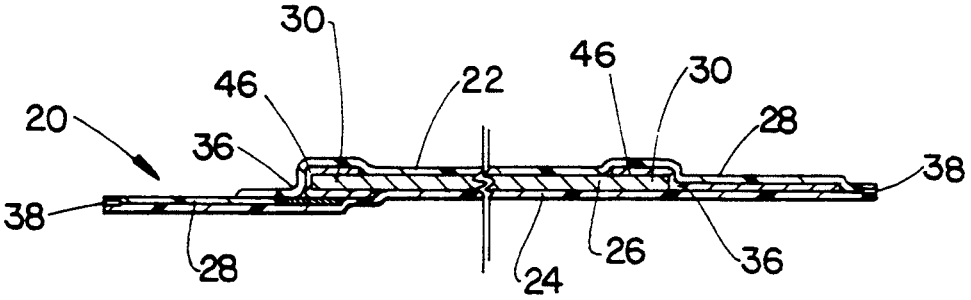
FIG. 4 is a vertical sectional view of FIG. 3, illustrating a different indicium attachment for each flap.

The partitions 46 may be juxtaposed with and joined, as shown, to the longitudinal side margins 30 of the sanitary napkin 20 adjacent the outboard edges of the absorbent core 26. More particularly, as illustrated in the left-hand side of FIG. 4, the partitions 46 may be joined to either the absorbent core 26, backsheet 24, or may be joined to and incorporated into the flap 28, as illustrated in the right-hand side of FIG. 4.

If the partition 46 is interposed between the topsheet 22 and backsheet 24 of the flap 28, the partition 46 may be joined to either or both of the topsheet 22 and backsheet 24. Alternatively, the partition 46 may wrap the absorbent core 26, and be interposed between the absorbent core 26 and the backsheet 24. This is a configuration similar to that of FIG. 2, and in such configuration the partition 46 may be joined to either or both of the absorbent core 26 and the backsheet 24.

If desired, the indicia 46 may be integral with either the topsheet 22, the backsheet 24, or the absorbent core 26. This may be accomplished by printing the indicia 46 onto the inwardly facing surface of either the topsheet 22, of the backsheet 24, or upon either major surface of the absorbent core 26. It is, however, generally preferred that the indicia 46 not be printed onto the backsheet 24 or the face of the absorbent core 26 oriented towards the backsheet 24, so that the indicia 46 may be more easily seen through the topsheet 22 and not blocked or obscured by the absorbent core 26, particularly if a light or pastel colored indicia 46 is selected.

The indicia 46 may be printed in any pattern desired, with the aforementioned and aforeillustrated design which is convex towards the longitudinal centerline 34 being generally preferred. Printed indicia 46 may be used with either the flapped sanitary napkin 20 of FIGS. 3 and 4, a sanitary napkin 20 according to FIGS. 1 and 2 without flaps 28, or other absorbent articles as hereinafter discussed. The indicia 46 may be printed onto any of the aforementioned components of the sanitary napkin 20 by a gravure system as is well known in the art and may be printed using inks or dyes. A particularly preferred material for the printed indicia 46 is Pontamine Fast Scarlet 48 liquid dye sold by the Mobay Chemical Corporation of Union, New Jersey.

If it is desired, the discrete indicia 46 and the absorbent core 26 may be of the same color. For example, referring to FIG. 5, the indicia 46 and the absorbent core 26 may be of a different thickness presenting an appearance to the user of a significant change in elevation. Alternatively, the indicia 46 may not have a significant difference in elevation than the absorbent core 26 but may merely present a roughened texture or coarser topography to the user. If a difference in elevation is selected for the indicia 46, this structure may be accomplished by providing indicia 46 and an absorbent core 26 of different thicknesses. Preferably, the indicia 46 are of lesser density than the absorbent core 26. Therefore, generally the indicia 46 are thicker than the absorbent core 26, so that the indicia 46 may be formed, for example, by running the core 26 through a nip which compresses the core 26 to the desired thickness differential leaving indicia 46 in the uncompressed areas. This density difference prevents rapid wicking of loading through the indicia 46 and obviates rapid failure of the sanitary napkin 20 from occurring.

Figure 5:
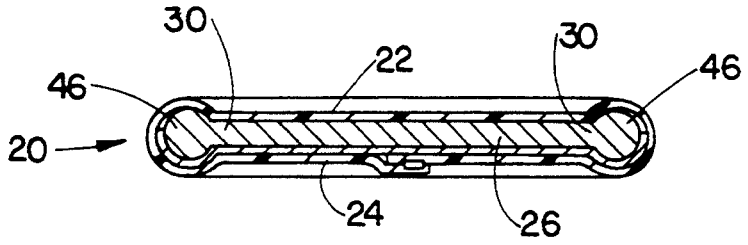
FIG. 5 is a vertical sectional view of a sanitary napkin according to the present invention having an absorbent core and indicia of differing elevations.

While the structure generally opposite that illustrated in FIG. 5 is feasible, i.e., an absorbent core 26 which is thicker than the indicia 46, such a structure is generally less preferred because typically the indicia 46 of such a structure will be of a higher density than the absorbent core 26. This structure presents the undesirable property that loading which has laterally migrated to the indicia 46 will generally rapidly penetrate the indicia 46 and cause failure of the sanitary napkin 20 before the wearer or caretaker becomes aware that the loading has reached the indicia 46.

If desired, the indicia 46 and the absorbent core 26 may be used in conjunction with absorbent articles other than sanitary napkins 20. For example and referring to FIGS. 6 and 7, the claimed means 46 for alerting a wearer or caretaker to the incipient failure of an absorbent core 26 may be advantageously used in an execution of a disposable diaper 20'. Such a diaper 20' has a topsheet 22, backsheet 24, and absorbent core 26 generally in accord with those described above. However, the diaper 20' is shaped to be worn about the hips and lower torso of a wearer. Further, the disposable diaper 20' typically comprises a means for maintaining such a wearing arrangement about the hips and lower torso of a wearer. Adhesive tapes 50 have long been advantageously used for this purpose. Adhesive tapes 50 made in accordance with commonly assigned U.S. Pat. No. 3,848,594 issued Nov. 19, 1974 to Buell, which patent is incorporated herein by reference for the purpose of showing a particularly preferred adhesive tape 50 structure, are suitable. Generally, a disposable diaper may be made in accordance with commonly assigned U.S. Pat. No. 3,860,003 issued Jan. 14, 1975 to Buell is preferred, which patent is incorporated herein by reference for the purpose of showing a particularly suitable and well known method of constructing a disposable diaper 20'.

Figure 6:
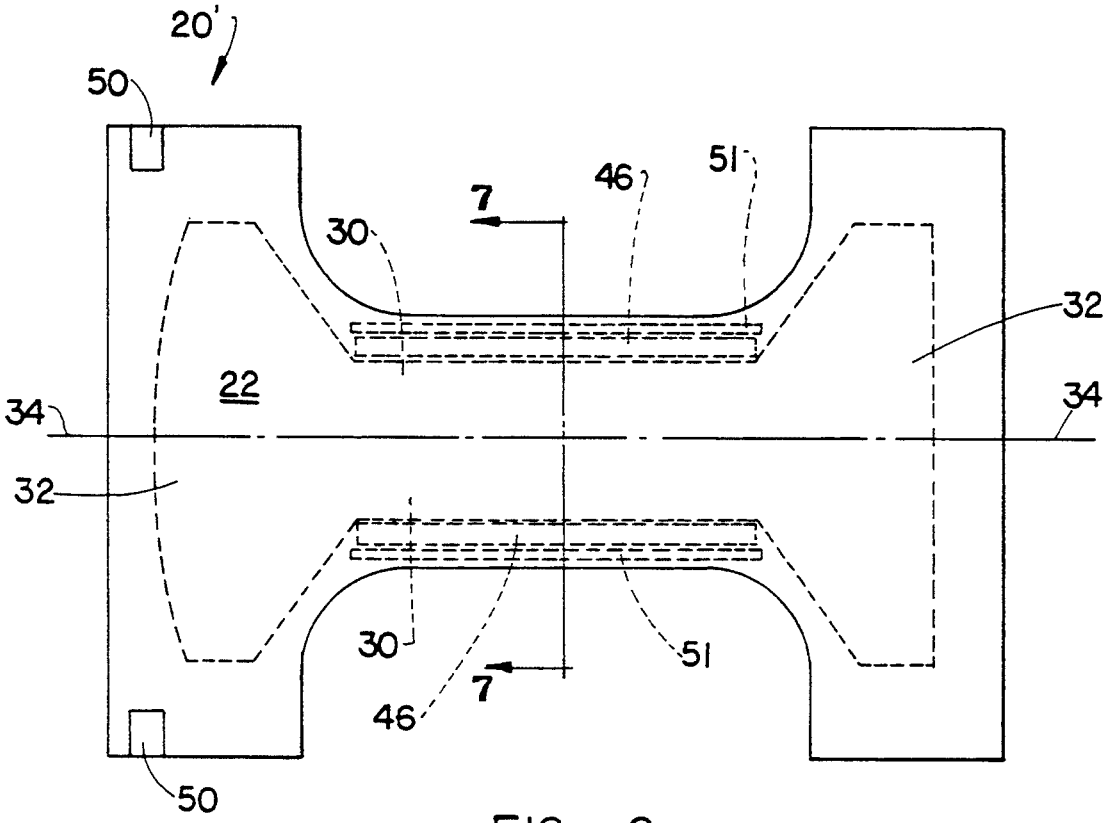
FIG. 6 is a top plan view of a diaper having discrete separate indicia laterally outboard of the core.

Referring to FIG. 6, if desired, the indicia 46 and absorbent core 26 may be discrete, separate components. This may be accomplished by providing indicia 46 of a thickness generally equivalent that of the absorbent core 26 and disposing an indicium 46 laterally outboard of the absorbent core 26. Each indicium 46 may be joined to the backsheet 24, the topsheet 22, or the longitudinal side margins 30 of the absorbent core 26, any combination thereof, or may be merely juxtaposed with the longitudinal side margins 30 of the absorbent core 26.

Figure 7:
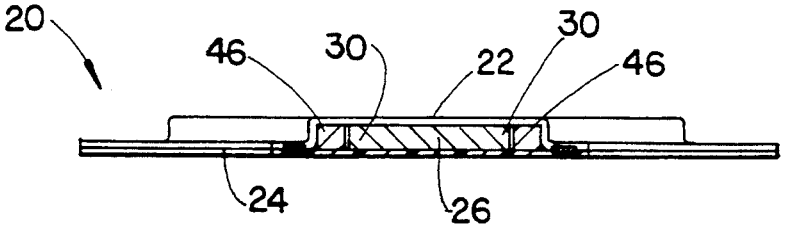
FIG. 7 is a vertical sectional view taken along line 6—6 of FIG. 6.

As illustrated in FIG. 7, any arrangement in which the indicia 46 are laterally outboard of the core 26 and the wearer or caretaker can visually detect the presence of loading at the indicia 46 prior to the perimeter of the absorbent article 20 being reached by such loading is suitable. The indicia 46 may be of substantially the same color as the absorbent core 26, or preferably, contrast in color with the absorbent core 26.

Suitable materials for separate indicia 46 include cellulose fluff, similar to that used for the absorbent core 26, 28 grams per square meter (17 pounds per 3,000 square feet) basis weight tissue manufactured according to U.S. Pat. No. 3,301,746 issued Jan. 31, 1967 to Sanford et al. and 24 or 52 grams per square square meter (15 or 32 pounds per 3,000 square feet) basis weight Spec 10 tissue manufactured by the James River Corporation of Green Bay, Wisconsin. Preferably separate indicia 46 do not have AGM so that the principal absorbent capacity of the diaper 20' remains laterally centered.

It will be apparent to one skilled in the art that any of the foregoing illustrated indicia 46 may likewise be advantageously used in an execution of an adult incontinence product (not shown). Several adult incontinence products are well known in the art and comprise two-piece and multicomponent systems having detachable belts, briefs, and other forms of undergarments. Adult incontinence products may be made by appropriately scaling the aforementioned infant diapers 20' or may be made according to the teachings of U.S. Pat. No. B1 4,490,148 issued Nov. 18, 1986 to Beckestrom, which patent is incorporated herein by reference for the purpose of disclosing an alternate embodiment of an adult incontinence product. The claimed indicia 46 may be used in any such execution.

If the indicia 46 are not a separate element, but rather are incorporated into the backsheet 24, as described above, the indicia.46 may either differ in color from the topsheet 22 or may present a different appearance to the wearer or caretaker through a topography or texture difference.

Such a color, topographical, or texture difference may be accomplished by providing a backsheet 24 which is of a substantially different material than the topsheet 22. For example, the backsheet 24 may be made of a nonwoven material instead of the aforementioned polyolefinic film. A liquid impervious laminate of a nonwoven material, such as Sontara Style 8407 material, sold by the DuPont Company of Wilmington, Delaware, has been found sufficiently discernible from the aforementioned formed film topsheet 22 to allow approaching absorbed bodily fluid to be easily visually detected. The indicia 46 are formed by providing longitudinally oriented strips of the different backsheet 24 material laterally outboard of the absorbent core 26 and outside of the topsheet 22.

It will be apparent to one skilled in the art that various combinations and permutations of the foregoing indicia 46 are feasible. For example, an absorbent article, such as a disposable diaper 20', sanitary napkin 20, or adult incontinence product, may have both the partitions 46 and a core 26 with indicia 46 of a different topography or texture than that of the absorbent core 26. It will be apparent to one skilled in the art that various other combinations are feasible, all of which are within the scope of the claimed invention.

What is claimed is:

1. A disposable absorbent article for absorbing liquids and having a longitudinal centerline and two longitudinal side margins, said article comprising:

a liquid pervious topsheet;

a liquid impervious backsheet joined to said topsheet;

a generally planar absorbent core positioned between said topsheet and said backsheet, said core having a top surface a bottom surface, and two longitudinal side edges; and a liquid previous means for visually indicating when liquid has approached the longitudinal side margins of said disposable absorbent article, said means comprising two visually discernible indicia disposed between said topsheet and said backsheet, wherein one indicium is disposed along each said longitudinal side edge of said absorbent core and being in contact with and in liquid communication with the longitudinal side edge of said absorbent core at points located between the top surface and bottom surfac of said absorbent core.

2. The absorbent article of claim 1 wherein said indicia have a different elevation relative to said planar absorbent core, said indicia being unfolded, and having a greater thickness than said absorbent core.

3. The absorbent article of claim 2 wherein said indicia are integral with said absorbent core.

4. A disposable diaper for absorbing liquids and having a longitudinal centerline and two longitudinal side margins, said article comprising:

a liquid pervious topsheet;

a liquid impervious backsheet joined to said topsheet;

a generally planar absorbent core positioned between said topsheet and said backsheet, said core having a top surface, a bottom surface, and two longitudinal side edges; and a liquid pervious means for visually indicating when liquid has approached the longitudinal side margins of said diaper, said means comprising two visually discernible indicia disposed between said topsheet and said backsheet, wherein one indicium is disposed along each said longitudinal side edge of said absorbent core and being in contact with and in liquid communication with the longitudinal side edge of said absorbent core at points located between the top surface and bottom surface of said absorbent core.

5. A Disposable absorbent article according to claim 4, wherein said indicia are absorbent.

6. A disposable adult incontinence product for absorbing liquids and having a longitudinal centerline and two longitudinal side margins, said article comprising:

a liquid pervious topsheet;

a liquid impervious backsheet joined to said topsheet;

a generally planar absorbent core positioned between said topsheet and said backsheet, said core having a top surface, a bottom surface, and two longitudinal side edges; and a liquid pervious means for visually indicating when liquid has approached the longitudinal side margins of said incontinence product, said means comprising two visually discernible indicia disposed between said top sheet and said backsheet, wherein one indicium is disposed along each said longitudinal side edge of said absorbent core and being in contact with and in liquid communication with the longitudinal side edge of said absorbent core at points located between the top surface and bottom surface of said absorbent core.

7. A disposable absorbent article according to claim 6, wherein said indicia are absorbent.

* * * * *